United States Patent
Fritz

(10) Patent No.: US 11,492,309 B2
(45) Date of Patent: Nov. 8, 2022

(54) METHOD AND SYSTEM FOR OBTAINING A BUTYLENE PRODUCT

(71) Applicant: LINDE GmbH, Pullach (DE)

(72) Inventor: Helmut Fritz, Munich (DE)

(73) Assignee: LINDE GmbH, Pullach (DE)

(*) Notice: Subject to any disclaimer, the term of this patent is extended or adjusted under 35 U.S.C. 154(b) by 0 days.

(21) Appl. No.: 17/433,870

(22) PCT Filed: Feb. 26, 2020

(86) PCT No.: PCT/EP2020/055054
§ 371 (c)(1),
(2) Date: Aug. 25, 2021

(87) PCT Pub. No.: WO2020/174016
PCT Pub. Date: Sep. 3, 2020

(65) Prior Publication Data
US 2022/0144727 A1 May 12, 2022

(30) Foreign Application Priority Data
Feb. 26, 2019 (EP) ..................................... 19159439

(51) Int. Cl.
*C07C 5/333* (2006.01)
*C07C 7/144* (2006.01)

(52) U.S. Cl.
CPC ............ *C07C 5/3337* (2013.01); *C07C 7/144* (2013.01)

(58) Field of Classification Search
CPC ............................... C07C 5/3337; C07C 7/144
See application file for complete search history.

(56) References Cited

U.S. PATENT DOCUMENTS

| 5,430,218 A | 7/1995 | Miller et al. |
| 2015/0158795 A1 | 6/2015 | Wynn et al. |

FOREIGN PATENT DOCUMENTS

EP 0568303 A2 11/1993

OTHER PUBLICATIONS

International Patent Application No. PCT/EP2020/055054 International Search Report and Written Opinion of the International Searching Authority dated Apr. 22, 2020, 9 pages.

(Continued)

*Primary Examiner* — Thuan D Dang
(74) *Attorney, Agent, or Firm* — Lathrop GPM LLP

(57) ABSTRACT

The present invention concerns a process (100) for the production of a butylene product (9) in which a component mixture (2) containing butane, butylene and hydrogen is provided using a butane dehydrogenation (10) to which a reaction feed (1) containing butane and hydrogen is subjected, the component mixture (2) or part thereof being subjected as a first separation feed to a first membrane separation (40), by means of which a first permeate (3) enriched in hydrogen with respect to the first separation feed and a first retentate (4) depleted in hydrogen with respect to the first separation feed and containing hydrogen, butane and butylene are formed, the first retentate (4) or part thereof being subjected to a second membrane separation (50) as a second separation feed, in which a second permeate (6) containing at least the predominant part of the hydrogen of the second separation feed and a second retentate containing at least the predominant part of the butane and the butylene of the second separation feed are formed, wherein the first membrane separation (40) is carried out using a sweep gas (5) containing butane and the first permeate (3) is obtained as permeate (3) charged with butane of the sweep gas (5) and/or the second membrane separation (50) is carried out (Continued)

using the sweep gas (5) containing butane and the second permeate (6) is obtained as permeate (6) charged with butane of the sweep gas (5), and wherein the first permeate (3) charged with butane of the sweep gas (5) and/or the second permeate (3) charged with butane of the sweep gas or one or more parts thereof is used in the formation of the reaction feed (1). A corresponding plant is also the subject of this invention.

14 Claims, 1 Drawing Sheet

(56) References Cited

OTHER PUBLICATIONS

English Translation of International Patent Application No. PCT/EP2020/055054 International Search Report dated Apr. 22, 2020, 2 pages.
Gulf Cooperation Council Patent Application No. GC 2020-39253 Examination Report dated Aug. 10, 2021, 5 pages.
International Patent Application No. PCT/EP2020/055054 International Preliminary Report on Patentability dated Mar. 12, 2021, 5 pages.
English Translation of International Patent Application No. PCT/EP2020/055054 International Preliminary Report on Patentability dated Mar. 12, 2021, 5 pages.

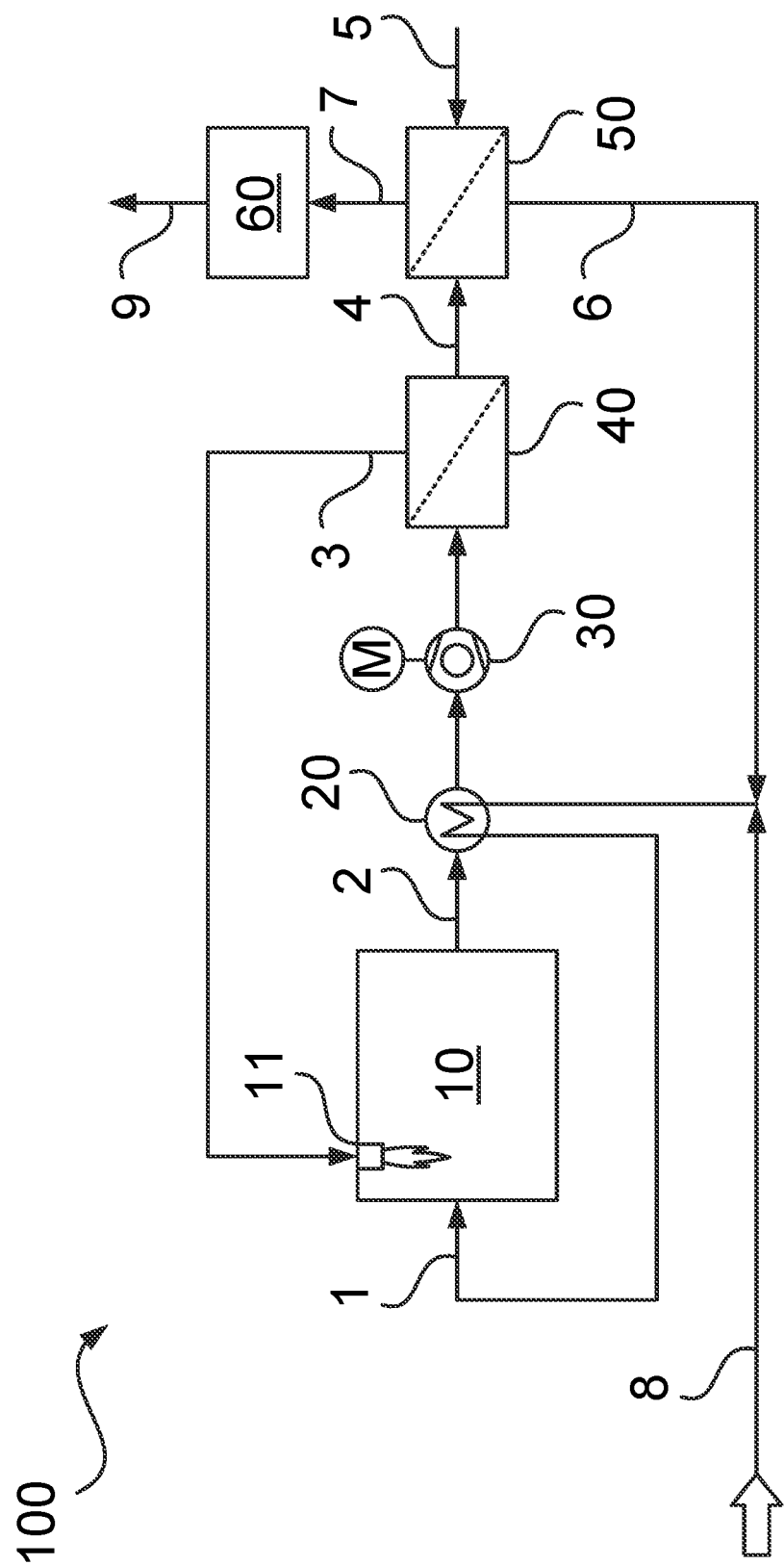

METHOD AND SYSTEM FOR OBTAINING A BUTYLENE PRODUCT

The invention relates to a method and a plant for the manufacture of a butylene product according to the preambles of the independent claims.

PRIOR ART

Butylenes (butenes; in the following only the term "butylene" is used in the singular, irrespective of the butylene isomers that may be present) are traditionally produced predominantly by steam cracking of hydrocarbon feedstocks and other conversion methods in refinery processes. In these cases, butylene is a by-product, which is present but only in comparatively small quantities, however. An alternative process for the production of butylenes is butane dehydrogenation.

Butane (catalytic) dehydrogenation is a well known process in the petrochemical industry that has certain common features to propane dehydrogenation, as described in the article "Propene" in Ullmann's Encyclopedia of Industrial Chemistry, online edition 16 Sep. 2013, DOI: 10.1002/14356007.a22_211.pub3, in particular Section 3.3.1, "Propane Dehydrogenation".

Like propane dehydrogenation, butane dehydrogenation is an endothermic equilibrium reaction generally carried out on noble or heavy metal catalysts, such as platinum or chromium. The dehydration reaction is highly selective. For commercially available processes, total yields of approx. 90% are cited. Notwithstanding this high selectivity, smaller quantities of hydrocarbons with one, two and three, as well as more than four carbon atoms as by-products are typically produced in addition to the cleaved off hydrogen. These by-products as well as butane not converted during butane dehydrogenation must be separated to obtain a butylene product.

Steam cracking processes and refinery processes in which butylene is formed are also extensively described in literature, for example in the article "Ethylene" in Ullmann's Encyclopedia of Industrial Chemistry, online publication 15 Apr. 2009, DOI: 10.1002/14356007.a10_045.pub3, and in the article "Oil Refining" in Ullmann's Encyclopedia of Industrial Chemistry, online publication 15 Jan. 2007, DOI: 10.1002/14356007.a18_051.pub2.

In steam cracking processes and refinery processes, butylene-containing component mixtures are also formed and they must be processed accordingly to obtain a butylene product. This invention is basically suitable for all processes and plants in which component mixtures are formed which contain butylene and in particular components boiling lower than butylene.

In commercial butane dehydrogenation plants, the processing of a corresponding component mixture typically involves the cryogenic separation of hydrocarbons with two carbon atoms and higher-boiling compounds from hydrocarbons with three or more carbon atoms (so-called deethanization) after appropriate preparation, e.g. compression and carbon dioxide removal. Further separation steps include the formation of a fraction predominantly or exclusively containing butane and butylene and the separation of this fraction. Comparable processes are also used to process component mixtures formed in steam cracking processes and refinery processes.

The cryogenic processes known from the prior art for processing corresponding component mixtures are characterised by an rather high investment expenditure, which results in particular from the machines for cold generation and the apparatus for cold transmission. Due to the (positive) economy of scale, the cryogenic processes for large capacity plants are the separation processes of choice. However, for plants with lower capacity, the specific investment costs for cryogenic processes increase disproportionately.

There is therefore a need for alternatives to the separation processing of butylene and component mixtures containing components with a lower boiling point than butylene, especially if these component mixtures are produced in a butane dehydrogenation process and in comparatively small quantities.

DISCLOSURE OF THE INVENTION

Against this background, the present invention proposes a method and a plant for the production of butylene with the respective characteristics of the independent patent claims. Preferred embodiments are the subject of the dependent patent claims as well as the following description.

Fluids of any kind are generally referred to here as "rich" in one or more components contained if the content of the one or more components is at least 50%, 60%, 70%, 80%, 90%, 95%, 99% or 99.5% on a molar, weight or volume basis. They are referred to as "poor" in one or more components when the content of one or more components is no more than 30%, 20%, 10%, 5%, 1% or 0.5% on a molar, weight or volume basis. They can be "enriched" or "depleted" on one or more components in the language used here, wherein these terms refer to a corresponding content in a source fluid from which the respective fluid was formed. The fluid is referred to as enriched if it contains at least 2, 5, 10, 100 or 1,000 times the content of the one or more components relative to the source fluid. However, the fluid is considered depleted if it contains at most 0.5 times, 0.1 times, 0.01 times or 0.001 times the content of the one or more components relative to the source fluid. A fluid "predominantly" containing one or more components is rich in this or these as defined above.

A fluid (the term fluid is also used to refer to corresponding flows, fractions, etc.) is derived from, or formed from, another fluid (also referred to here as an initial fluid) if it has at least some components contained in, or obtained from, the initial fluid. A fluid derived or formed in this sense may be obtained or formed from the initial fluid by separating or branching a portion or one or more components, enriching or depleting with respect to one or more components, chemically or physically reacting one or more components, heating, cooling, pressurizing and the like. A material flow can also be formed, for example, simply by withdrawing it from a storage tank or separating it from another material flow.

In the following, the terms "pressure level" and "temperature level" are used to characterize pressures and temperatures, whereby it shall be expressed that pressures and temperatures do not have to be available in the form of exact pressure or temperature values. For example, a pressure level or temperature level can be ±1%, 5%, 10%, 20% or 50% around an average value. Multiple pressure and temperature levels can represent disjunctive or overlapping areas. The same pressure or temperature level may still exist, for example, if pressures and temperatures have been reduced due to pipe losses or cooling. The pressure levels indicated here in bar are absolute pressures.

This invention is based in particular on the knowledge that known membrane separation processes (practically) have no economies of scale, which is why they are generally not economical solutions for high plant capacities, but often cost-effective solutions for small plants. Membrane separation processes differ fundamentally from cryogenic distillation processes typically in that they are only suitable for coarse (bulk) separations, but cannot supply high-purity products.

Against this background, the present invention now proposes a simple and cost-effective process for separating a butylene-containing fraction or a butylene product from a component mixture formed using butane dehydrogenation, wherein the component mixture is formed particularly in comparatively small production quantities or the butane dehydrogenation has comparatively low production capacity. A "small production quantity" or a "small production capacity" is here understood to mean a production quantity of 20 to 120 kta (kilotons per year), in particular 35 to 80 kta, for example approx. 50 kta.

The separation proposed in the context of this invention proves to be considerably more advantageous than conventional cryogenic separation sequences, particularly with regard to the investment costs for correspondingly low production capacities, since complex apparatus and machines can be dispensed with. At the same time, as will be explained in detail below, a reaction feed can be provided within the framework of the present invention in the separation which contains butane and hydrogen in quantities suitable for butane dehydrogenation. External dosing can therefore be dispensed with.

This invention is particularly suitable for use in smaller butane dehydrogenation plants which can be retrofitted to increase production in existing plants, such as steam cracking plants. Due to the proposed hydrogen separation according to the invention, the remaining gas mixtures can be processed in such existing plants or the separation facilities provided there and do not overload them. No further retrofitting measures are therefore necessary.

The present invention proposes, as a whole, a process for the production of a butylene product in which a butane, butylene and hydrogen containing component mixture is provided using butane dehydrogenation to which a butane and hydrogen containing reaction feed is subjected. As already mentioned above, the inventive process can be integrated into an overall process or a plant in which further material-converting process steps and separation steps are carried out, for example one or more steam cracking steps and separation steps assigned to them. The butylene product produced in accordance with the invention can also be obtained in particular by using corresponding further separation steps.

The present invention provides that the component mixture or a part thereof is subjected as a first separation feed to a first membrane separation, by means of which a first permeate enriched in hydrogen as compared to the first separation feed and a first retentate containing hydrogen, butane and butylene depleted in hydrogen as compared to the first separation feed are formed. It is advantageous that the first permeate contains no or only small amounts of butane and butylene, which are contained in the first separation feed fed to the first membrane separation. As mentioned above, membrane separation processes are typically not designed to achieve a complete separation of components, so that the first retentate still contains significant amounts of hydrogen contained in the first separation feed. For its further separation, the second membrane separation described below is used.

The first (and subsequently explained second) membrane separation can be carried out within the context of the present invention using membrane separation equipment known from the art. For further details reference is made to technical literature.

A "permeate" is understood here to be a gas or gas mixture which predominantly or exclusively contains components which are not or predominantly not retained by a membrane used in a membrane separation stage, i.e. which pass unhindered through the membrane (essentially or at least preferably). Accordingly, a "retentate" is a gas or gas mixture that contains predominantly or exclusively components that are completely or at least predominantly retained by the membrane in the membrane separation stage.

In the present invention, the first retentate or part thereof is subjected as a second separation feed to a second membrane separation in which a second permeate containing at least the major part of the hydrogen of the second separation feed and a second retentate containing at least the major part of the butane and the butylene of the second separation feed are formed. In the second membrane separation, in other words, the hydrogen from the second separation feed is predominantly or completely removed, so that a retentate containing essentially heavier components, in particular butane and butylene, is formed. This second retentate can then be further processed to obtain the butylene product.

Within the context of this invention, two different alternatives may be used, which are advantageous depending on the circumstances. This means that the first membrane separation can be carried out using a sweep gas containing butane and the first permeate can be obtained as permeate charged with butane from the sweep gas. A corresponding sweep gas is guided along the membrane used in the membrane separation on the permeate side and enables a larger quantity or a larger proportion to be obtained across the membrane, since lighter components passing through the membrane can be continuously carried off and thus a concentration or partial pressure gradient across the membrane can be maintained. As the butane-containing sweep gas, butane or a gas or gas mixture rich in butane, but in any case advantageously low in hydrogen or free therefrom, is used in particular, in order to achieve the aforementioned advantageous effects in membrane separation. In any case, the butane in the permeate to which the butane of the sweep gas is applied comes from the sweep gas, and not or only in small proportions from the first separation feed.

Alternatively or additionally, it is also possible within the scope of the present invention to carry out the second membrane separation using the sweep gas containing butane and thus to obtain the second permeate as permeate charged with butane of the sweep gas. In this respect, what was said above in relation to the use of the sweep gas containing butane in the first membrane separation essentially also applies.

Finally, the present invention provides for the use of the first permeate charged with butane of the sweep gas and/or the second permeate charged with butane of the sweep gas, or one or more parts thereof, in the formation of the reaction feed. However, if one of the permeates, i.e. the first or second permeate, is not obtained as a permeate charged with butane of the sweep gas, i.e. if no corresponding sweep gas is used in the corresponding first or second membrane separation, this is typically not used in the formation of the reaction feed but, as explained below, is underfired in one or more reactors or fed to a fuel gas network in a corresponding plant.

The particular advantage of using a permeate charged with butane of a butane-containing sweep gas in the formation of the reaction feed is that the corresponding permeate charged with butane already contains the components required in a corresponding reaction feed, butane and hydrogen, and therefore does not have to be added separately. In the context of the present invention, the double advantage of using the sweep gas is that the corresponding membrane separation can be advantageously influenced and at the same time a gas mixture can be provided that can be used directly in a separation application. In particular, because the hydrogen provided in a corresponding reaction application does not originate from external sources but from a membrane separation, additional, possibly otherwise necessary cleaning steps can be dispensed with.

In the context of this invention, the reaction feed subjected to butane dehydrogenation contains in particular 45 to 95 volume percent butane and 1 to 50 volume percent hydrogen. An appropriate proportion of hydrogen may advantageously be partially or completely covered by the hydrogen passing into the permeate used in the membrane separation step(s) in accordance with the invention.

The component mixture formed in butane dehydrogenation and the first separation feed advantageously contain 40 to 60 volume percent butane, 20 to 30 volume percent butylene and 25 to 30 volume percent hydrogen. In butane dehydrogenation, additional (excess) hydrogen is thus formed which, in the proportion in which it is not returned to butane dehydrogenation, can be used advantageously for other purposes.

In the first membrane separation, as already mentioned, a partial depletion of the first separation feed of hydrogen takes place, so that the first retentate and the second separation feed in the context of the present invention contain in particular 10 to 20 volume percent hydrogen.

The use of the second membrane separation results in a further hydrogen depletion, so that the second retentate has only small proportions of hydrogen of 5 to 15 volume percent hydrogen.

It is advantageous that in the process according to the invention the component mixture or its part subjected to the first membrane separation is subjected to cooling and compression before it is subjected to the membrane separation. Cooling takes place in particular by heat exchange with the reaction feed or part thereof before it is subjected to butane dehydrogenation. In this configuration, the process proposed in accordance with the invention permits particularly advantageous heat recovery.

The compression of the component mixture or its part subjected to the first membrane separation is advantageously carried out within the scope of the present invention at a pressure level of 2 to 38 bar, 6 to 20 bar, 8 to 18 bar, 10 to 14 bar, 10 to 16 bar or 12 to 14 bar. This pressure level depends in particular on the required delivery pressure of the second retentate or on a required inlet pressure of the process(es) to which the second retentate is to be subjected. The pressure level also depends on the volume fraction of the hydrogen in the component mixture from butane dehydrogenation, because the advantageous separation pressure in the first and second membrane separation again depends on a corresponding volume fraction. Furthermore, if hydrogen or a hydrogen-rich fraction is obtained as permeate in the first and second membrane separation, the pressure level is to be used for heat recovery even after the required pressure has been reached, especially if a feed into a heating gas network is to take place. A further influencing factor is the outside temperature, because hydrocarbons with three and possibly more carbon atoms should not condense in the first and second membrane separation. Depending on the design of the membranes used in the first and second membrane separation steps, an accompanying heating may also be advantageous depending on the partial pressure of the corresponding components. Finally, another pressure influencing factor is the compressor used. Advantageously, this should not have more than two intercooling stages.

A compressor driven by an electric motor, in particular a three-stage turbo compressor, is advantageously used as a compressor, since the electric drive saves complex turbines and an equally complex steam system connection.

The feed-in of the second retentate in the further process step(s), in particular for steam cracking or one or more of these downstream separation steps, is advantageously carried out at a pressure level of 1 to 38 bar, so that no further compression steps are necessary if the compression of the raw gas from the butane dehydrogenation is suitably selected.

In particular, the present invention allows only the first membrane separation to be carried out using the sweep gas containing butane and thus only the first permeate to be obtained as a permeate charged with butane from the sweep gas. Alternatively, only the second membrane separation can be carried out using the sweep gas containing butane and only the second permeate can be obtained as permeate charged with butane of the sweep gas. In both cases, the permeate not charged with butane of the sweep gas or part of it may be burned for heating in one or more reactors used for butane dehydrogenation. For this purpose, for example, a feed into a heating gas network can take place, as already mentioned. Alternatively, it is also possible to use a corresponding permeate containing in particular predominantly or exclusively hydrogen for a different purpose. In any case, in this way the hydrogen formed in butane dehydrogenation can be used advantageously.

The permeate not charged with butane of the sweep gas is advantageously provided at a pressure level of 3 to 7 bar for appropriate use in the respective first or second membrane separation and in this way can in particular be fed into a heating gas network operated at an appropriate pressure level.

This invention also provides a plant, the characteristics of which are specified in the corresponding independent patent claim. With regard to the features and advantages of the inventionally proposed plant, reference is made explicitly to the features and advantages already described with regard to the method explained above and to features and advantages explained for its advantageous embodiments. The same applies in particular to a plant in accordance with a particularly preferred embodiment of the present invention, which has means which have been set up to carry out a corresponding procedure.

The invention is explained in more detail below with reference to the attached drawings, which illustrate a preferred form of the present invention.

SHORT DESCRIPTION OF THE DRAWINGS

FIG. 1 illustrates a method designed according to an embodiment of the invention in a highly simplified, schematic representation.

DETAILED DESCRIPTION OF THE DRAWINGS

FIG. 1 illustrates a method designed according to an embodiment of the invention in a highly simplified, schematic representation and is designated 100 in total.

In the method 100 one or more reactors are used which are equipped for butane dehydrogenation 10 and to which a butane-containing reaction feed 1 is fed. The reactor or reactors is or are heated by one or more burners.

A component mixture 2 containing butane, butylene and hydrogen is formed by means of the reactor or reactors, and therefore using the butane dehydrogenation 10 carried out therein, and is provided therewith in the process 100. The production quantity, for example, is approx. 50 kta. The component mixture 2, or only a part of the component mixture 2, is subjected to a cooling process 20 and in particular to a heat exchange with the input mixture 1.

After the cooling 20 or cooling, the component mixture 2 or its part subjected to the cooling, or again only a part thereof, is subjected to compression 30, wherein in particular a three-stage turbo compressor driven by means of an electric motor M can be used in a housing enclosing the three compressor stages. The compression takes place in particular at a pressure level of 12 to 15 bar.

After compression 30, the component mixture or its part subjected to compression 30, or again only part of it, is subjected to a first membrane separation 40 as the first separation feed. In this example, a first permeate 3 enriched with hydrogen compared to the first separation feed and poor or free in butane and butylene and a first retentate 4 depleted in hydrogen compared to the first separation but still containing hydrogen and otherwise containing butane and butylene feed are formed. In the example shown, the first membrane separation is carried out without using a sweep gas containing butane and thus the first permeate 3 is not obtained as a permeate charged with butane of a sweep gas. However, as explained above, procedural variants in which exactly this is done are also being considered.

In the example shown, membrane separation 40 is carried out in such a way that a pressure level at which the first permeate 3 is obtained is just high enough that the first permeate 3, or only part of it, can be fed to the burner(s) 11 without further compression and used as a heating gas in the burner(s). If a quantity of the first permeate 3 is not sufficient for heating by means of the burner or burners 11, it may in particular be provided to sweep the first membrane separation 30 with a combustible sweep gas, in particular methane, or a gas mixture containing methane, in particular with natural gas. The first permeate 3 can also be fed into a heating gas network of a corresponding plant or a corresponding plant group.

The first retentate 4, or only a part thereof, is subjected as a second separation feed to a second membrane separation 50, in which a sweep gas 5 containing at least the predominant part of the hydrogen contained in the second separation feed and a second permeate 6 containing at least the predominant part of the hydrogen contained in the second separation feed and a second retentate 7 containing at least the predominant part of the butane and the butylene from the second separation feed are formed, in comparison with the second separation feed, using a butane containing sweep gas 5. The sweep gas 5 is used in particular so that a sufficient, i.e. complete or essentially complete, hydrogen separation can take place irrespective of the reduction of the hydrogen partial pressure already achieved in the first membrane separation.

The second permeate 6 comprises butane of the sweep gas 5 and hydrogen from the second separation feed due to the described formation in the second membrane separation 50. In the example shown, the second permeate 6 is thus obtained as a permeate charged with butane of the sweep gas 5. The second permeate 6, or only part of it, can therefore be recycled in a particularly advantageous way as part of reaction feed 1 to the reactor(s) 10, since the butane dehydrogenation carried out there typically uses reaction feeds containing a certain proportion of hydrogen. Reference is made to the above explanations for other embodiments.

Therefore, the second membrane separation can be used in the context of the present invention both for the separation of hydrogen to obtain a butylene product and for the addition of hydrogen to a reaction feed 1. The second permeate 6, or the part of it returned to the reactor or reactors 10 as part of the reaction feed 1, in particular a fresh feed 8 containing predominantly or exclusively butane is added here.

In the example shown, the second retentate 7 is added to one or more further process steps 60, in particular the separation of butane and butylene and, if necessary, the separation of heavier components. In the further process step(s) 60, in addition to one or more other fractions not separately illustrated here, in particular a butylene product 9 containing predominantly or exclusively butylene may be formed. Furthermore, a fraction containing mainly or exclusively butane can also be obtained in the further process step(s), which can be used as the sweep gas 5. The further process step(s) 60 can be part of a steam cracking process with respectively assigned separation steps.

The invention claimed is:

1. A method (100) for producing a butylene product (9) in which, using a butane dehydrogenation (10) to which a reaction feed (1) containing butane and hydrogen is subjected, a component mixture (2) containing butane, butylene and hydrogen is provided, wherein the component mixture (2) or a part thereof is subjected as a first separation feed to a first membrane separation (40) by means of which a first permeate (3) enriched in hydrogen with respect to the first separation feed and a first retentate (4) depleted in hydrogen with respect to the first separation feed and containing hydrogen, butane and butylene are formed, wherein the first retentate (4) or a part thereof is subjected as a second separation feed to a second membrane separation (50) in which a second permeate (6) containing at least the major part of the hydrogen of the second separation feed and a second retentate containing at least the major part of the butane and the butylene of the second separation feed are formed, wherein the first membrane separation (40) is carried out using a sweep gas (5) containing butane, the first permeate (3) being obtained as a permeate (3) charged which butane of the sweep gas (5) and/or the second membrane separation (50) is carried out using the sweep gas (5) containing butane and the second permeate (6) being obtained as a permeate (6) charged with butane of the sweep gas (5), wherein the first permeate (3) charged with butane of the sweep gas (5) and/or the second permeate (6) charged with butane of the sweep gas or one or more parts thereof are used in the formation of the reaction feed (1), wherein the sweep gas (5) is guided along the membrane used in the membrane separation on the permeate side.

2. The method according to claim 1, wherein the reaction feed (1) comprises 45 to 95 volume percent butane and 1 to 50 volume percent hydrogen.

3. The method according to claim 1, wherein the component mixture (2) and the first separation feed comprise 40 to 60 volume percent butane, 20 to 30 volume percent butylene and 25 to 30 volume percent hydrogen.

4. The method according to claim 1, wherein the first retentate and the second separation feed comprise 10 to 20 volume percent hydrogen.

5. The method according to claim 1, wherein the second retentate comprises 5 to 15 volume percent hydrogen.

6. The method according to claim 1, wherein the component mixture (2) or its part subjected to the first membrane separation (40) is subjected to a cooling (20) and a compression (30) before being subjected to the membrane separation (40).

7. The method according to claim 6, wherein the compression (30) is carried out at a pressure level of 2 to 38 bar.

8. The method according to claim 6, wherein the compression (30) is carried out using one or more multi-stage turbo compressors, in particular with two or fewer intercooling stages.

9. The method according to claim 1, wherein the second retentate or a part thereof, in particular at a pressure level of 1 to 38 bar, is fed to one or more further process steps (60).

10. The method according to claim 9, wherein the further process step or steps (60) comprises a steam cracking process or one or more separation steps associated with the steam cracking process.

11. The method according to claim 9, wherein only the first membrane separation (40) is carried out using the sweep gas (5) containing butane and only the first permeate (3) is obtained as permeate (3) charged with butane of the sweep gas (5), or in which only the second membrane separation (50) is carried out using the sweep gas (5) containing butane and only the second permeate (6) is obtained as permeate (6) charged with butane of the sweep gas (5), in which the permeate (3, 6) or part thereof, which is in each case not charged with butane of the sweep gas (5), is combusted for heating in one or more reactors used for the butane dehydrogenation (10).

12. The method according to claim 11, wherein the permeate (3, 6) not charged with butane of the sweep gas (5) is provided in the membrane separation (40, 50) at a pressure level of 3 to 7 bar.

13. A plant for the production of a butylene product (9), comprising one or more reactors adapted to provide a component mixture (2) containing butane, butylene and hydrogen using a butane dehydrogenation (10) to which a reaction feed (1) containing butane and hydrogen is subjected, means arranged to subject the component mixture (2) or a part thereof as a first separation feed to a first membrane separation (40) by means of which a first permeate (3) enriched in hydrogen with respect to the first separation feed and a first retentate (4) depleted in hydrogen with respect to the first separation feed and containing hydrogen, butane and butylene are formed, means adapted to subject the first retentate (4) or a part thereof as a second separation feed to a second membrane separation (50) in which a second permeate (6) containing at least the major part of the hydrogen of the second separation feed and the butane of the sweep gas and a second retentate containing at least the major part of the butane and the butylene of the second separation feed are formed, means arranged to perform the first membrane separation (40) using a sweep gas (5) containing butane and to obtain the first permeate (3) as a permeate (3) charged with butane of the sweep gas (5) and/or to perform the second membrane separation (50) using the sweep gas (5) containing butane and to obtain the second permeate (6) as a permeate (6) charged with butane of the sweep gas (5), means adapted to use the first permeate (3) charged with butane of the sweep gas (5) and/or the second permeate (6) or one or more parts thereof charged with butane of the sweep gas in forming the reaction feed (1), wherein the sweep gas (5) is guided along the membrane used in the membrane separation on the permeate side.

14. The plant according to claim 13, which is arranged to perform a method (100) for producing a butylene product (9) in which, using a butane dehydrogenation (10) to which a reaction feed (1) containing butane and hydrogen is subjected, a component mixture (2) containing butane, butylene and hydrogen is provided, wherein the component mixture (2) or a part thereof is subjected as a first separation feed to a first membrane separation (40) by means of which a first permeate (3) enriched in hydrogen with respect to the first separation feed and a first retentate (4) depleted in hydrogen with respect to the first separation feed and containing hydrogen, butane and butylene are formed, wherein the first retentate (4) or a part thereof is subjected as a second separation feed to a second membrane separation (50) in which a second permeate (6) containing at least the major part of the hydrogen of the second separation feed and a second retentate containing at least the major part of the butane and the butylene of the second separation feed are formed, wherein the first membrane separation (40) is carried out using a sweep gas (5) containing butane, the first permeate (3) being obtained as a permeate (3) charged which butane of the sweep gas (5) and/or the second membrane separation (50) is carried out using the sweep gas (5) containing butane and the second permeate (6) being obtained as a permeate (6) charged with butane of the sweep gas (5), wherein the first permeate (3) charged with butane of the sweep gas (5) and/or the second permeate (6) charged with butane of the sweep gas or one or more parts thereof are used in the formation of the reaction feed (1).

* * * * *